US00PP22218P2

(12) United States Plant Patent
Ferguson

(10) Patent No.: US PP22,218 P2
(45) Date of Patent: Nov. 1, 2011

(54) STRAWBERRY PLANT NAMED 'DRISSTRAWSEVENTEEN'

(50) Latin Name: *Fragaria×ananassa*
Varietal Denomination: DrisStrawSeventeen

(75) Inventor: Michael D. Ferguson, Moorpark, CA (US)

(73) Assignee: Driscoll Strawberry Associates, Inc, Watsonville, CA (US)

( * ) Notice: Subject to any disclaimer, the term of this patent is extended or adjusted under 35 U.S.C. 154(b) by 0 days.

(21) Appl. No.: 12/803,582

(22) Filed: Jun. 30, 2010

(51) Int. Cl.
*A01H 5/00* (2006.01)

(52) U.S. Cl. ..... Plt./209

(58) Field of Classification Search ..... Plt./209
See application file for complete search history.

*Primary Examiner* — Annette Para

(74) *Attorney, Agent, or Firm* — Jondle & Associates, P.C.

(57) ABSTRACT

This invention relates to a new and distinct variety of strawberry plant named 'DrisStrawSeventeen'. The new variety is primarily characterized by an upright and globose plant habit, very strong vigor, and very large-sized berries, is disclosed.

3 Drawing Sheets

Genus and species: *Fragaria×ananassa.*
Variety denomination: 'DrisStrawSeventeen'.

BACKGROUND OF THE NEW PLANT

The present invention relates to a new and distinct strawberry variety designated 'DrisStrawSeventeen' and botanically known as *Fragaria×ananassa.* This new strawberry variety was discovered in Ventura County, Calif. in October 2006 and originated from a cross between the proprietary female parent '13H377' (unpatented) and the proprietary male parent '119J176' (unpatented). The original seedling of the new variety was first asexually propagated at a nursery in Shasta County, Calif. in October 2005.

'DrisStrawSeventeen' was subsequently asexually propagated at a nursery in Shasta County, Calif. and underwent further testing in Ventura County, Calif. for three years (2006-2009). The present invention has been found to retain its distinctive characteristics through successive asexual propagations via stolons and tissue culture.

Plant Breeder's Rights for this variety have not been applied for. 'DrisStrawSeventeen' has not been made publicly available or sold more than one year prior to the filing date of this application.

DESCRIPTION OF THE PHOTOGRAPHS

The accompanying color photographs show typical specimens of the new variety at various stages of development. The colors shown are as true as can be reasonably obtained by conventional photographic procedures. The photographs were taken from three-month-old plants.

DESCRIPTION OF THE NEW VARIETY

Figure 1:
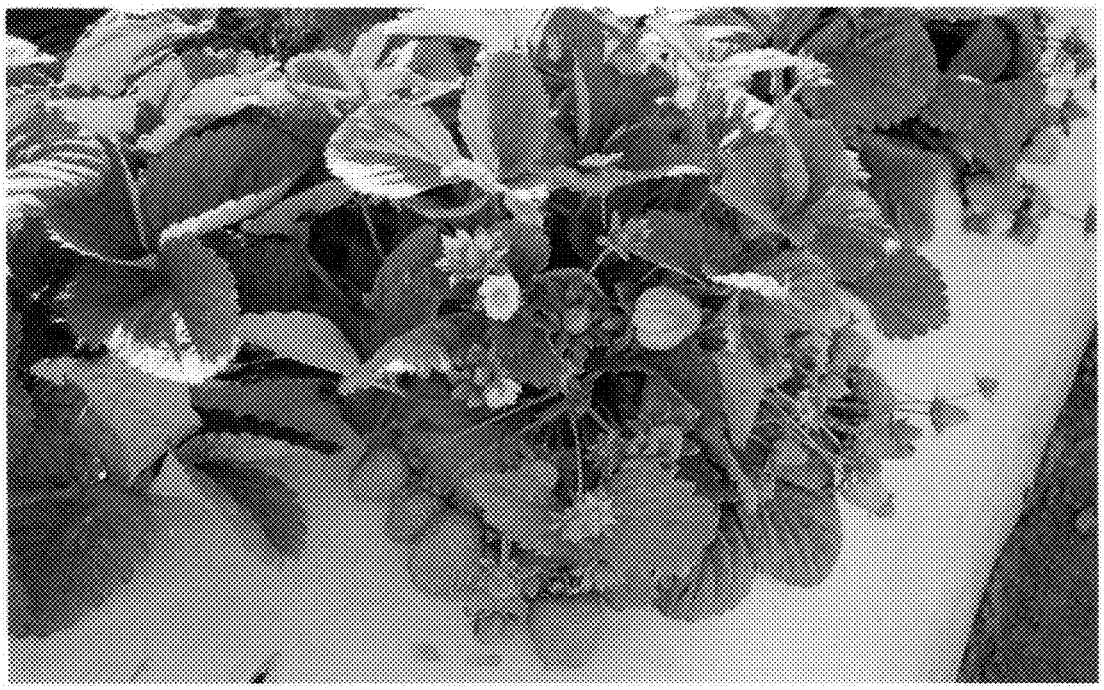
FIG. 1 shows overall plant habit including fruit at various stages of development.
Figure 2:
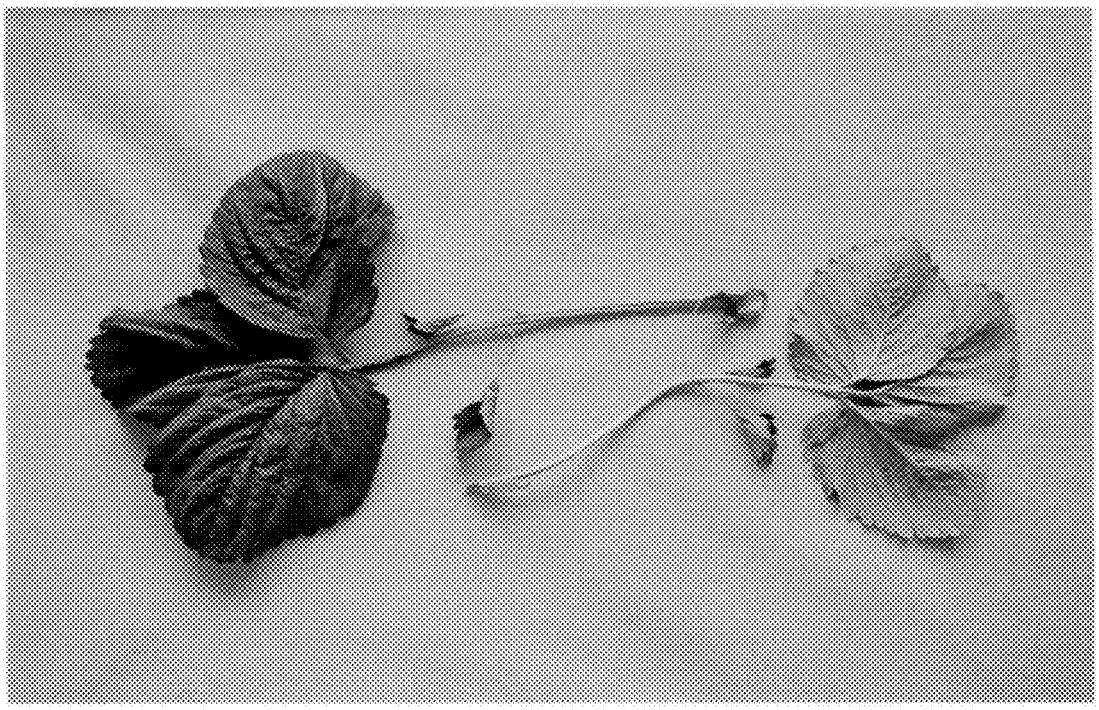
FIG. 2 shows leaves of the plant with three leaflets.
Figure 3:
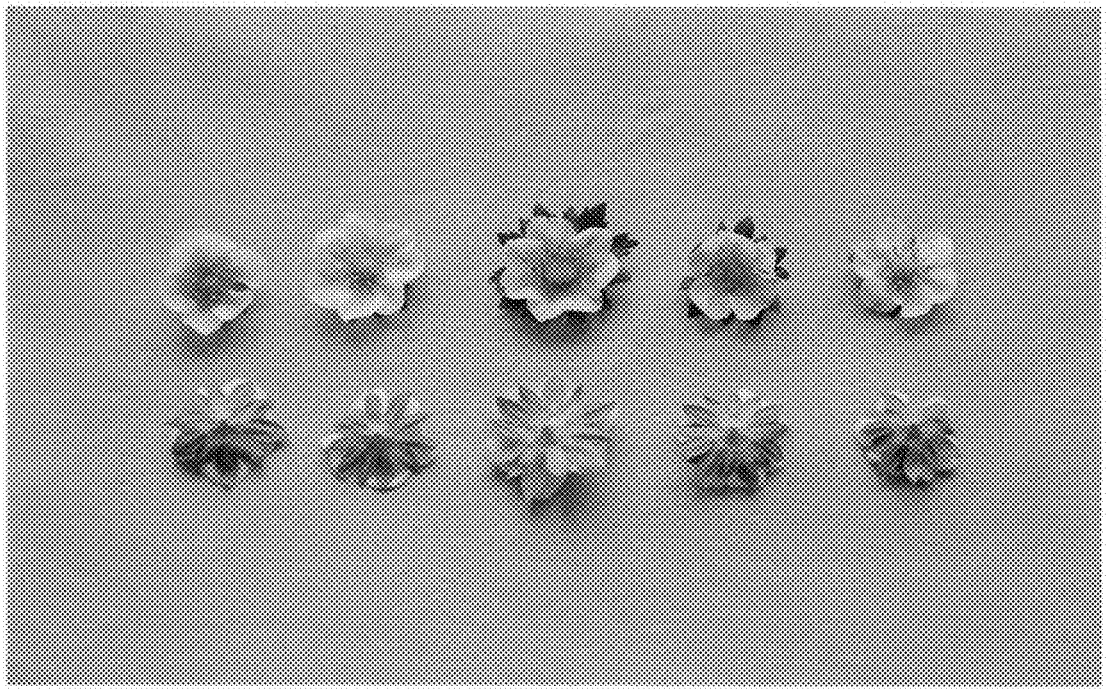
FIG. 3 shows both the upper surface and lower surface of several of the flowers.
Figure 4:
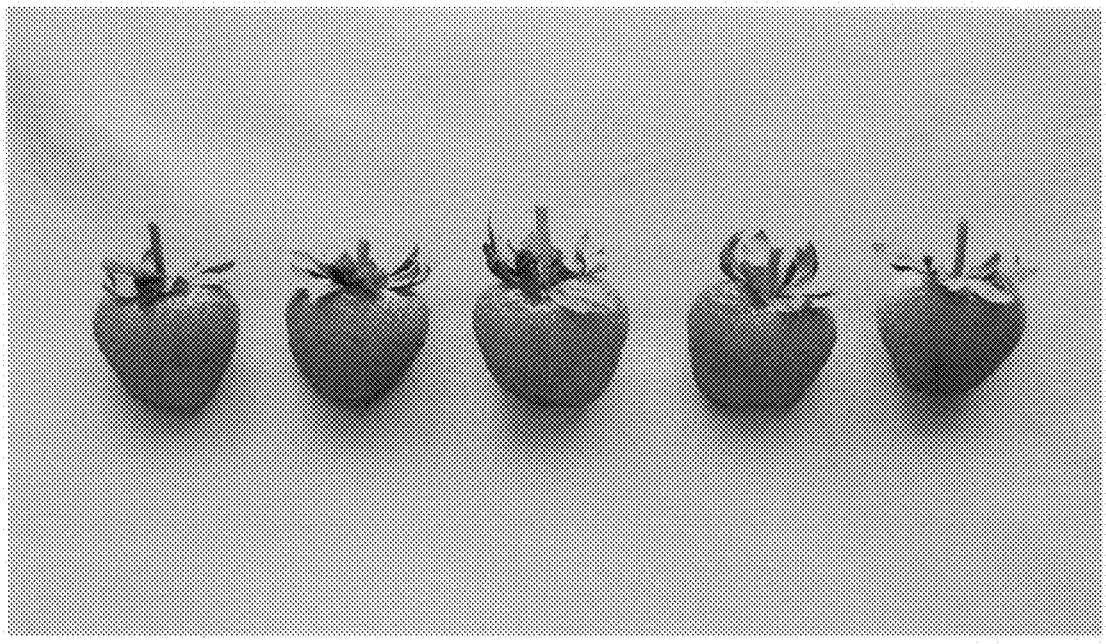
FIG. 4 shows the whole fruit.
Figure 5:
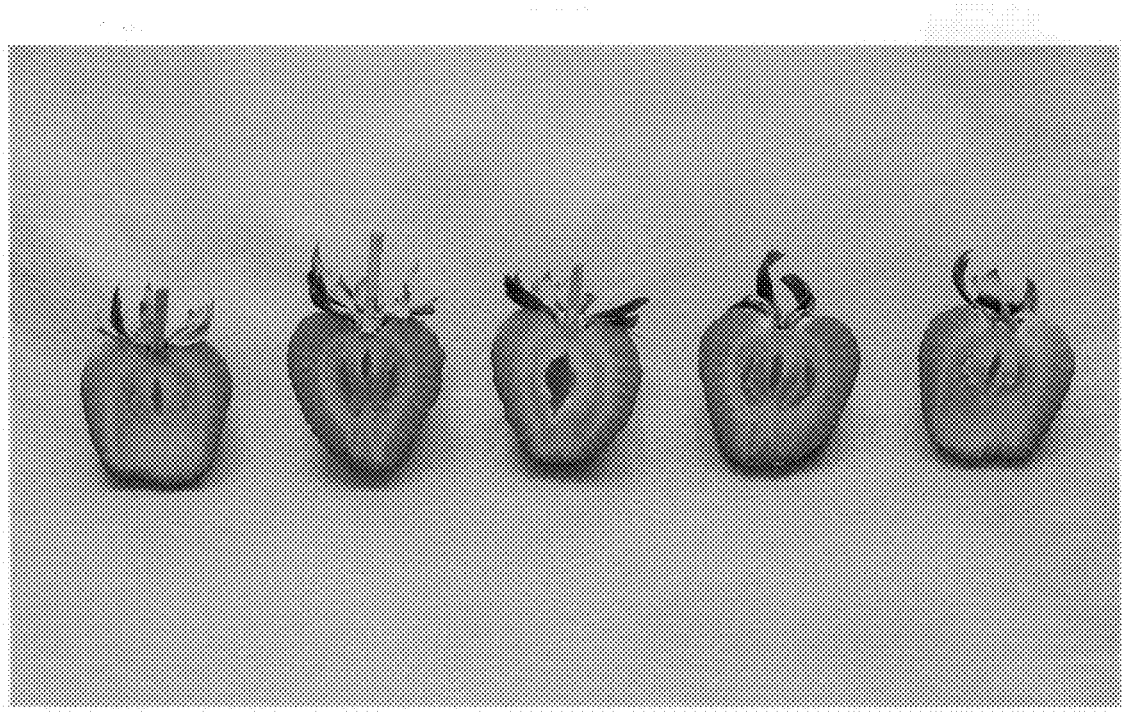
FIG. 5 shows the fruit in longitudinal cross-section.

The following detailed descriptions set forth the distinctive characteristics of 'DrisStrawSeventeen'. The data which define these characteristics is based on observations taken in Ventura County, Calif. from 2006 to 2009. This description is in accordance with UPOV terminology. Color designations, color descriptions, and other phenotypical descriptions may deviate from the stated values and descriptions depending upon variation in environmental, seasonal, climatic, and cultural conditions. 'DrisStrawSeventeen' has not been observed under all possible environmental conditions. The botanical description of 'DrisStrawSeventeen' was taken from four-month-old plants. Color terminology follows The Royal Horticultural Society Colour Chart, London (R.H.S.) (2001).

DETAILED BOTANICAL DESCRIPTION OF THE PLANT

Classification:
- *Species.*—*Fragaria×ananassa.*
- *Common name.*—Strawberry.
- *Denomination.*—'DrisStrawSeventeen'.

Parentage:
- *Female parent.*—The proprietary female parent '13H377' (unpatented).
- *Male parent.*—The proprietary male parent '119J176' (unpatented).

Plant:
- *Height.*—30.8 cm.
- *Diameter.*—50.7 cm.
- *Number of crowns/plant.*—3.
- *Habit.*—Upright and globose.
- *Density of individual plant.*—Dense.
- *Vigor.*—Very strong.

Leaves:
- *Terminal leaflet length.*—9.8 cm.
- *Terminal leaflet width.*—9.0 cm.
- *Terminal leaflet length/width ratio.*—1.1.
- *Number of teeth/terminal leaflet.*—24.
- *Shape of teeth.*—Obtuse.
- *Color.*—Upper surface: RHS 137A (Dark green). Lower surface: RHS 148B (Medium yellow-green).
- *Leaf shape in cross section.*—Concave.
- *Leaf blistering.*—Medium.
- *Leaf glossiness.*—Medium.
- *Number of leaflets.*—3 only.
- *Terminal leaflet margin profile.*—Revolute.

*Terminal leaflet length/width ratio.*—As long as broad.
*Terminal leaflet shape.*—Orbicular.
*Terminal leaflet base shape.*—Rounded.
*Terminal leaflet apex shape.*—Rounded.
*Petiole.*—Length: 18.9 cm. Diameter: 0.316 cm. Pubescence: Medium. Pose of hairs: Upwards. Color: RHS 145A (Medium yellow-green).

Petiolule:
*Color.*—RHS 145A (Medium yellow-green).
*Length.*—1.361 cm.
*Diameter.*—0.178 cm.

Stipule:
*Length.*—2.8 cm.
*Width.*—0.793 cm.
*Pubescence.*—Medium.
*Stipule anthocyanin coloration.*—Weak; RHS 145C (Light yellow-green).

Stolon:
*Number.*—Few.
*Average number of daughter plants per plant.*—34.
*Stolon anthocyanin.*—RHS 63B (Medium red-purple).
*Thickness.*—Medium.
*Pubescence.*—Medium.

Inflorescence:
*Position relative to foliage.*—Beneath.
*Time of flowering* (*50% of plants at first flower*).—Medium.
*Flower size.*—Medium.
*Diameter.*—2.966 cm.
*Petals.*—Shape: Orbicular. Apex: Rounded. Base: Concave-convex. Margin: Entire. Spacing: Overlapping. Length: 1.286 cm. Width: 1.330 cm. Length/width ratio: 1.0; as long as broad. Typical and observed petal number per flower: 6. Color (both surfaces): RHS 155C (White).
*Calyx.*—Diameter: 3.234 cm. Diameter relative to corolla: Same size. Inner calyx diameter relative to outer: Same size.
*Sepal.*—Shape: Elliptical. Apex: Convex. Margin: Entire. Length: 1.244 cm. Width: 0.579 cm. Typical and observed sepal number per flower: 13.
*Receptacle color.*—RHS 1C (Light green-yellow).
*Anther color.*—RHS 22A (Medium yellow-orange).

Fruiting Truss:
*Length.*—19.5 cm; long.
*Diameter at base of truss.*—0.383 cm.
*Number of berries per fruiting truss.*—5.
*Attitude at first picking.*—Prostrate.
*Color at base of truss.*—RHS 144B (Medium yellow-green).

Fruit:
*Length.*—4.902 cm.
*Width.*—4.690 cm.
*Length/width ratio.*—1.0.
*Fruit hollow length.*—1.876 cm.
*Fruit hollow width.*—1.625 cm.
*Fruit hollow length/width ration.*—1.2.
*Fruit hollow center* (*size*).—Medium.
*Weight* (*per individual berry*).—28.4 g.
*Fruit ratio of length/maximum width.*—As broad as long.
*Relative fruit size.*—Very large.
*Predominant fruit shape.*—Wedged.
*Difference in shape between primary and secondary fruits.*—None or very slight.
*Unevenness of fruit surface.*—Strong.
*Fruit skin color.*—RHS 46B (Dark red).
*Evenness of fruit color.*—Uneven.
*Fruit glossiness.*—Medium.
*Insertion of achenes.*—Level with surface.
*Achene coloration* (*sunward side of berry*).—RHS 166D (Medium greyed-orange).
*Achene coloration* (*shaded side of berry*).—RHS 163C (Light greyed-orange).
*Achenes per berry.*—390.
*Band without achenes.*—Narrow.
*Insertion of calyx.*—Level.
*Pose of calyx segments.*—Reflexed.
*Size of calyx in relation to fruit.*—Between smaller and same size.
*Adherence of calyx.*—Strong.
*Firmness of flesh.*—Firm.
*Color of flesh.*—RHS N155D (White) and RHS N30A (Medium orange-red).
*Evenness of flesh color.*—Slightly uneven.
*Distribution of flesh color.*—Marginal and central.
*Sweetness.*—Medium.
*Acidity.*—Medium.
*Texture when tasted.*—Coarse.
*Type of bearing.*—Fully everbearing.
*Grams of fruit/plant.*—486 g.
*Harvest interval.*—Early June to late December.
*Harvest maturity.*—Mid-season.

Disease, pest, and stress resistance:
*Botrytis fruit rot.*—Moderately susceptible.
*Powdery mildew.*—Moderately susceptible.
*Tetranychus urticae.*—Moderately resistant.
*Tarsonemus pallidus.*—Moderately resistant.
*Aphelencoides fragariae.*—Moderately resistant.
*Pratylenchus penetrans.*—Moderately resistant.
*Ditylenchus dipsac.*—Moderately resistant.
*Anthonomus rubi.*—Moderately resistant.
*Aphis spp.* (*Aphids*).—Moderately resistant.
*Lygus hesperus* (*Lygus bug*).—Moderately resistant.
*Wind.*—Moderately resistant.

COMPARISON WITH PARENTAL AND COMMERCIAL VARIETIES

When 'DrisStrawSeventeen' is compared to the proprietary female parent '13H377' (unpatented), 'DrisStrawSeventeen' has a more vigorous growth habit and a larger plant size than '13H377'. In addition, 'DrisStrawSeventeen' has lighter colored foliage, a larger fruit size, and a higher fruit yield than '13H377'.

When 'DrisStrawSeventeen' is compared to the proprietary male parent '119J176' (unpatented), 'DrisStrawSeventeen' has a stronger everbearing habit and is more susceptible to powdery mildew. In addition, 'DrisStrawSeventeen' has lighter colored foliage, a larger fruit size, and a higher fruit yield than '119J176'.

When 'DrisStrawSeventeen' is compared to the commercial variety 'DrisStrawThree' (U.S. Plant Pat. No. 19,673), the petiole pose of hairs for 'DrisStrawSeventeen' is upwards, while the petiole pose of hairs for 'DrisStrawThree' is outwards to downwards. In addition, 'DrisStrawSeventeen' has fruit with medium sweetness, coarse texture when tasted, and an uneven fruit color, while 'DrisStrawThree' has fruit with a strong sweetness, very fine texture when tasted, and a slightly uneven fruit color.

I claim:

1. A new and distinct variety of strawberry plant as described and shown herein.

* * * * *